United States Patent
Avegliano et al.

(10) Patent No.: US 10,318,875 B2
(45) Date of Patent: Jun. 11, 2019

(54) DISEASE PREDICTION AND PREVENTION USING CROWDSOURCED REPORTS OF ENVIRONMENTAL CONDITIONS

(71) Applicant: International Business Machines Corporation, Armonk, NY (US)

(72) Inventors: Priscilla Barreira Avegliano, São Paulo (BR); Carlos Henrique Cardonha, São Paulo (BR); Julio Nogima, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 712 days.

(21) Appl. No.: 14/961,863

(22) Filed: Dec. 7, 2015

(65) Prior Publication Data
US 2017/0161617 A1    Jun. 8, 2017

(51) Int. Cl.
  G06N 5/04    (2006.01)
  G06F 19/00   (2018.01)
  G16H 50/50   (2018.01)

(52) U.S. Cl.
  CPC ............ G06N 5/04 (2013.01); G06F 19/00 (2013.01); G16H 50/50 (2018.01); *Y02A 90/24* (2018.01); *Y02A 90/26* (2018.01)

(58) Field of Classification Search
  USPC .......................................................... 706/46
  See application file for complete search history.

(56) References Cited

U.S. PATENT DOCUMENTS 7,551,137 B2    6/2009  Gagnon
8,392,152 B2    3/2013  Rao
(Continued)

FOREIGN PATENT DOCUMENTS

CA    2611538 A1    6/2009
CA    2745519 A1    6/2010
(Continued)

OTHER PUBLICATIONS

Crowdsourcing, citizen sensing and sensor web technologies for public and environmental health surveillance and crisis management: trends, OGC standards and application examples, Kamel Boulos et al. International Journal of Health Geographics 2011, 10:67 pp. 1-29, Maged N Kamel Boulos et al.*
Elsevier Handbook of Statistics vol. 33, 2015, pp. 171-202 Chapter 8—Big Data Applications in Health Sciences and Epidemiology Saumyadipta Pyne, Anile Kumar S. Vullikanti, Madhav V. Marathe.*
EPJ Data Science Dec. 2017, Uncovering the relationships between military community health and affects expressed in social media Svitlana Volkova, Lauren E Charles, Josh Harrison, Courtney D Corley pp. 1-23.*
(Continued)

*Primary Examiner* — Michael B Holmes
(74) *Attorney, Agent, or Firm* — Grant Johnson; Otterstedt, Ellenbogen & Kammer, LLP.

(57) ABSTRACT

Embodiments of the invention provide techniques which utilize crowdsourced reports of environmental conditions to predict and/or prevent disease outbreaks. In one aspect, a method comprises receiving one or more crowdsourced reports about one or more environmental conditions; inferring one or more input parameters for at least one disease outbreak model based at least in part on the one or more crowdsourced reports; applying the at least one disease outbreak model to at least the one or more inferred parameters to predict one or more characteristics of at least one potential disease outbreak associated with the reported one or more environmental conditions; and, based at least in part on the predicted one or more characteristics, implementing one or more corrective actions to mitigate the at least one potential disease outbreak.

22 Claims, 3 Drawing Sheets

(56) References Cited

U.S. PATENT DOCUMENTS

| | | | |
|---|---|---|---|
| 8,805,707 | B2 | 8/2014 | Schumann, Jr. et al. |
| 9,503,489 | B2 * | 11/2016 | Dettori ................ H04L 65/4084 |
| 9,578,512 | B1 * | 2/2017 | Avegliano ............. H04W 8/005 |
| 9,633,334 | B2 * | 4/2017 | de Assuncao .......... G06Q 50/26 |
| 9,667,680 | B2 * | 5/2017 | Dettori ................ H04L 65/4084 |
| 9,723,043 | B2 * | 8/2017 | Dettori ................ H04L 65/4084 |
| 9,749,459 | B2 * | 8/2017 | Cardonha ......... H04M 1/72577 |
| 9,892,421 | B2 * | 2/2018 | Borger .............. G06Q 30/0246 |
| 9,898,754 | B2 * | 2/2018 | Borger .............. G06Q 30/0246 |
| 9,928,667 | B2 * | 3/2018 | Barreira Avegliano ..................... G07B 15/06 |
| 9,946,797 | B2 * | 4/2018 | Cardonha ......... G06F 17/30867 |
| 9,959,872 | B2 * | 5/2018 | Barreira Avegliano ..................... G10L 15/32 |
| 9,986,405 | B1 * | 5/2018 | Cardonha ............... H04W 4/70 |
| 10,033,781 | B2 * | 7/2018 | Dettori ................ H04L 65/4084 |
| 2009/0216747 | A1 * | 8/2009 | Li ........................ G06Q 10/067 |
| 2013/0253940 | A1 | 9/2013 | Zziwa |
| 2017/0308678 | A1 * | 10/2017 | Apreleva ................ G06F 19/00 |

FOREIGN PATENT DOCUMENTS

| | | |
|---|---|---|
| CN | 102818642 A | 12/2012 |
| WO | WO02/19246 A2 | 3/2002 |
| WO | WO2004/015612 A1 | 2/2004 |
| WO | WO2014/051824 A2 | 4/2014 |

OTHER PUBLICATIONS

Syafruddin & Noorani, "SEIR Model for Transmission of Dengue Fever in Selangor Malaysia," Int. J. Mod. Phys. Conf. Ser., 2012, v. 9, p. 380-389, World Sol. Pub. Co.

Buczak et al., "A data-driven epidemiological prediction method for dengue outbreaks using local and remote sensing data," BMC Medical Informatics and Decision Making, 2012, 12:124, pp. 1-20 , BioMed Central Ltd.

Kamel Boulos et al., "Crowdsourcing, citizen sensing and sensor web technologies for public and environmental health surveillance and crisis management: trends, OGC standards and application examples," International Journal of Health Geographics, 2011, 10:67, pp. 1-29, BioMed Central Ltd.

* cited by examiner

US 10,318,875 B2

DISEASE PREDICTION AND PREVENTION USING CROWDSOURCED REPORTS OF ENVIRONMENTAL CONDITIONS

BACKGROUND OF THE INVENTION

The present invention relates generally to the electrical, electronic and computer arts, and, more particularly, to techniques which utilize crowdsourced reports of environmental conditions to predict and/or prevent disease outbreaks.

Compartmental models are used in epidemiology to evaluate and predict disease outbreak. These models include SEIR models in which a human population is divided into four groups: Susceptible, Exposed, Infectious, or Recovered. An exemplary SEIR model is described in Syafruddin & Noorani, "SEIR Model for Transmission of Dengue Fever in Selangor Malaysia," Int. J. Mod. Phys. Conf. Ser., v. 9, p. 380-389, 2012, which is incorporated by reference herein.

The onset of some diseases may be associated with environmental factors. This is especially true for diseases that depend on transmission vectors such as insects or rodents. For example, in São Paulo, Brazil in early 2015, a serious drought caused people to store pluvial water, thus favoring the proliferation of mosquitos that transmit dengue fever. As a result, there was an increase of 57% on the number of reported cases of dengue fever in the region. Drought season in many regions of the world similarly stimulate citizens to store water at home, leading to potential outbreaks of mosquito-borne diseases such as dengue fever.

However, models of disease outbreak, such as SEIR, are based on information regarding the number of infected people and their location. Thus, while these models are able to predict spread of a disease among a population with reasonable accuracy, they require that the onset of the disease has already happened. Thus, disease outbreak models are useful to infer how an already existing disease will propagate (e.g., spread geographically) over time but are unable to predict the initial onset of disease.

BRIEF SUMMARY

Principles of the invention, in accordance with embodiments thereof, provide techniques which utilize crowdsourced reports of environmental conditions to predict and/or prevent disease outbreaks. In one aspect, a method comprises receiving one or more crowdsourced reports about one or more environmental conditions; inferring one or more input parameters for at least one disease outbreak model based at least in part on the one or more crowdsourced reports; applying the at least one disease outbreak model to at least the one or more inferred parameters to predict one or more characteristics of at least one potential disease outbreak associated with the reported one or more environmental conditions; and, based at least in part on the predicted one or more characteristics, implementing one or more corrective actions to mitigate the at least one potential disease outbreak.

In accordance with another embodiment of the invention, an apparatus includes a memory and at least one processor coupled to the memory. The processor is operative: to receive one or more crowdsourced reports about one or more environmental conditions; to infer one or more input parameters for at least one disease outbreak model based at least in part on the one or more crowdsourced reports; to apply the at least one disease outbreak model to at least the one or more inferred parameters to predict one or more characteristics of at least one potential disease outbreak associated with the reported one or more environmental conditions; and, based at least in part on the predicted one or more characteristics, to implement one or more corrective actions to mitigate the at least one potential disease outbreak.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWINGS

The following drawings are presented by way of example only and without limitation, wherein like reference numerals (when used) indicate corresponding elements throughout the several views, and wherein.

It is to be appreciated that elements in the figures are illustrated for simplicity and clarity. Common but well-understood elements that may be useful or necessary in a commercially feasible embodiment may not be shown in order to facilitate a less hindered view of the illustrated embodiments.

DETAILED DESCRIPTION

Embodiments of the present invention will be described herein in the context of illustrative methods and apparatus which utilize crowdsourced reports of environmental conditions to predict and/or prevent disease outbreaks. It is to be appreciated, however, that the invention is not limited to the specific apparatus and/or methods illustratively shown and described herein. Moreover, it will become apparent to those skilled in the art given the teachings herein that numerous modifications can be made to the embodiments shown that are within the scope of the claimed invention. Thus, no limitations with respect to the embodiments shown and described herein are intended or should be inferred.

Figure 1:
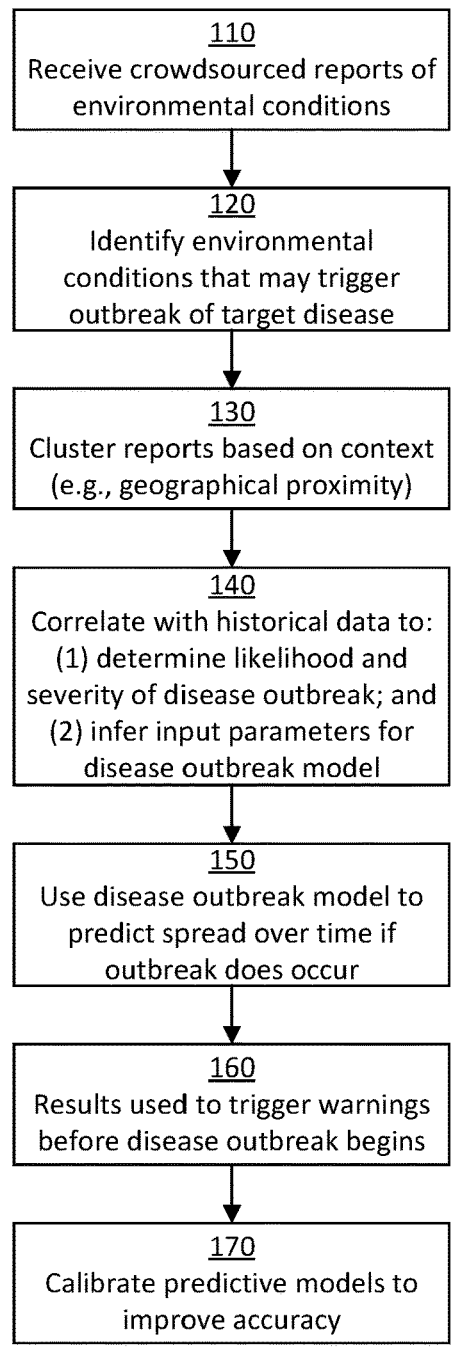
FIG. 1 is a flow diagram depicting at least a portion of an exemplary method according to an embodiment of the invention.

FIG. 1 is a flow diagram depicting at least a portion of an exemplary method according to an embodiment of the invention. In step 110, crowdsourced reports of environmental conditions, such as water puddles, are received. For example, citizens may report the locations (and other relevant information, such as the dimensions) of these environmental conditions using a client application on their mobile devices (i.e., a mobile app). A website and/or a telephone hotline (similar to New York City's 311) may additionally and/or alternatively be provided for citizens to report these environmental conditions. Other potentially relevant environmental conditions which may be reported by citizens include, for example, sightings of filth and/or vermin.

In step 120, the crowdsourced reports may be filtered to identify environmental conditions that may trigger outbreak of target diseases. For example, dengue fever is more likely to occur in the presence of environmental conditions such as water puddles and/or trash accumulation. In step 130, reports regarding relevant environmental conditions may be clustered based on similar contexts, such as geographic proximity.

In step 140, crowdsourced reports are correlated with historical data (e.g., regarding past disease outbreaks in a particular region) to estimate risks associated with a potential disease outbreak. This may involve predicting one or more of: a likelihood (i.e., probability) that a disease outbreak will occur, a time when a disease outbreak is most likely to occur, and/or a severity of a disease outbreak if it occurs (e.g., a number of people who would be affected).

These estimated risks, the crowdsourced reports, and/or the historical data may then be used to infer input parameters for a disease outbreak model. For example, this information could be provided to a SEIR model, such as that described in the aforementioned paper by Syafruddin & Noorani with reference to dengue fever. In step 150, the disease outbreak model is used with the inferred input parameters to predict the spread over time if an outbreak of the disease does occur.

In step 160, the results of the disease outbreak model are used to trigger warnings before the disease outbreak begins. For example, warnings may be broadcast in a targeted manner to populations who are determined to be likely to be affected by a potential disease outbreak. In one embodiment, these warnings may be provided to citizens through the aforementioned mobile app and/or through an emergency alert on their mobile phones. These warnings may also be provided to citizens through websites, automated telephone calls, media bulletins, and/or loudspeakers.

These warnings may also elicit corrective actions, such as the release (e.g., spraying) of one or more pesticides. These corrective actions may be performed in an automated and/or manual manner. Additionally and/or alternatively, the results may be displayed to system operators and/or public health authorities. For example, the display may include a (possibly animated) map showing if and how the disease is likely to spread over time.

In step 170, the predictive models are calibrated to improve their accuracy. For example, the predictions regarding the risks associated with a possible disease outbreak may be compared with the timing and/or severity of an actual disease outbreak. The historical data and/or predictive models may also be updated to reflect that a possible disease outbreak did not actually occur.

Figure 2:
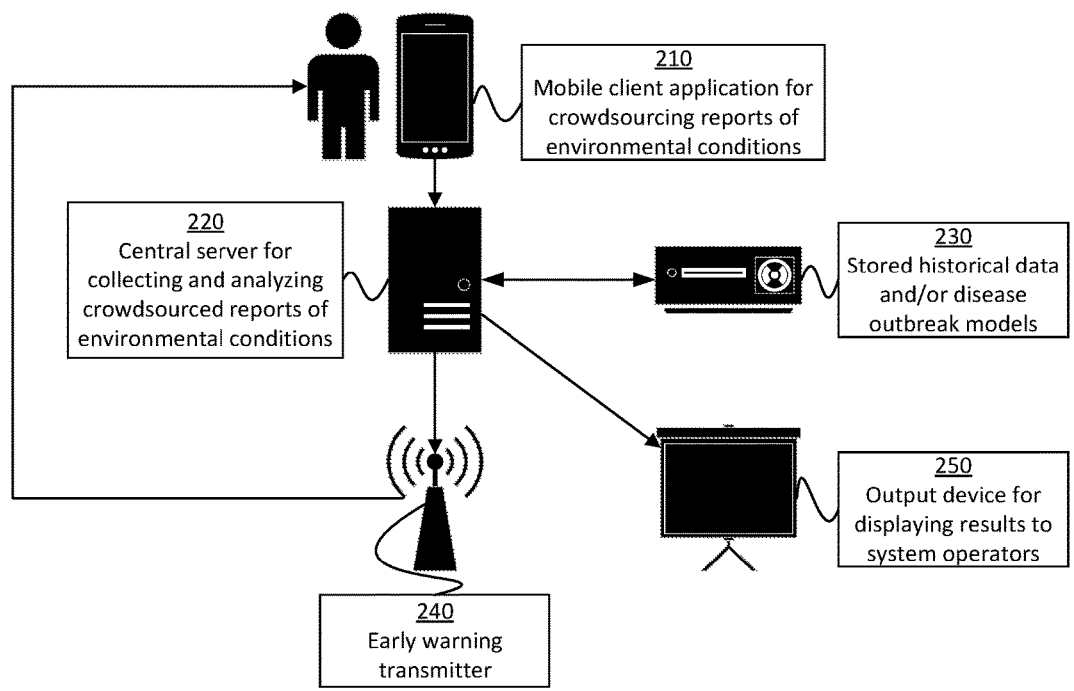
FIG. 2 is a block diagram depicting at least a portion of an exemplary system according to an embodiment of the invention.

FIG. 2 is a block diagram depicting at least a portion of an exemplary system according to an embodiment of the invention. Element 210 may represent a client application (e.g., executed on and/or accessible through a mobile phone or other computing device) for crowdsourcing reports of environmental conditions. As discussed above with reference to step 110 in FIG. 1, embodiments may additionally and/or alternatively include a website and/or a telephone hotline through which citizens can report environmental conditions.

Element 220 represents a central server for collecting and analyzing crowdsourced reports of environmental conditions. In illustrative embodiments, each of the steps in FIG. 1 is executed by central server 220, alone or in conjunction with the other elements shown in FIG. 2. For example, as discussed above, step 110 in FIG. 1 may involve client 210 in addition to server 220.

Element 230 represents storage for historical data and/or disease outbreak models. Storage 230 may be collocated with server 220; it may even be a component of server 220. Storage 230 may also be external to, or even remote from, server 220. Server 220 may read historical data and/or disease outbreak models from storage 230 in conjunction with the execution of, for example, steps 140 and/or 150 in FIG. 1. Server 220 may additionally and/or alternatively write to storage 230 (e.g., to update stored historical data and/or disease outbreak models) in conjunction with the execution of, for example, step 170 in FIG. 1.

Element 240 represents an early warning transmitter which may be used by server 220 in conjunction with the execution of step 160 in FIG. 1. Transmitter 240 may be collocated with server 220; it may even be a component of server 220. Transmitter 240 may also be external to, or even remote from, server 220. In some embodiments, transmitter 240 may communicate with client 210 to provide warnings to citizens. Additionally and/or alternatively, transmitter 240 may be used to order performance of automated and/or manual corrective actions. For example, transmitter 240 may be used to trigger an automated release (e.g., spraying) of one or more pesticides, or to instruct workers to remedy a reported environmental condition (e.g., to drain a water puddle and/or to collect accumulated trash).

Element 250 represents an output device for displaying results to system operators and/or public health officials in conjunction with the execution of step 160 in FIG. 1. Display 250 may be collocated with server 220; it may even be a component of server 220. Display 250 may also be external to, or even remote from, server 220. As discussed above with reference to step 160 in FIG. 1, display 250 may show a (possibly animated) map showing if and how a disease is likely to spread over time.

Although each of the elements is shown in FIG. 2 as a single component, it should be understood that any one of the elements may be implemented in a distributed manner. For example, element 210 may include a client application executed on mobile phones of a plurality of geographically dispersed citizens. Likewise, one or more of elements 220, 230, 240 and/or 250 may be implemented in a given embodiment as a plurality of geographically dispersed units. For example, it may be advantageous to implement element 240 using a distributed plurality of transmitters in order to improve transmission range and coverage. As another example, it may also be advantageous to implement elements 220 and/or 230 using a distributed plurality of servers in order to increase reliability.

Given the discussion thus far, it will be appreciated that, in general terms, an exemplary method according to an aspect of the invention comprises: receiving one or more crowdsourced reports about one or more environmental conditions; inferring one or more input parameters for at least one disease outbreak model based at least in part on the one or more crowdsourced reports; applying the at least one disease outbreak model to at least the one or more inferred parameters to predict one or more characteristics of at least one potential disease outbreak associated with the reported one or more environmental conditions; and, based at least in part on the predicted one or more characteristics, implementing one or more corrective actions to mitigate the at least one potential disease outbreak.

Exemplary System and Article of Manufacture Details

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

One or more embodiments of the invention, or elements thereof, can be implemented in the form of an apparatus including a memory and at least one processor that is coupled to the memory and operative to perform exemplary method steps.

Figure 3:
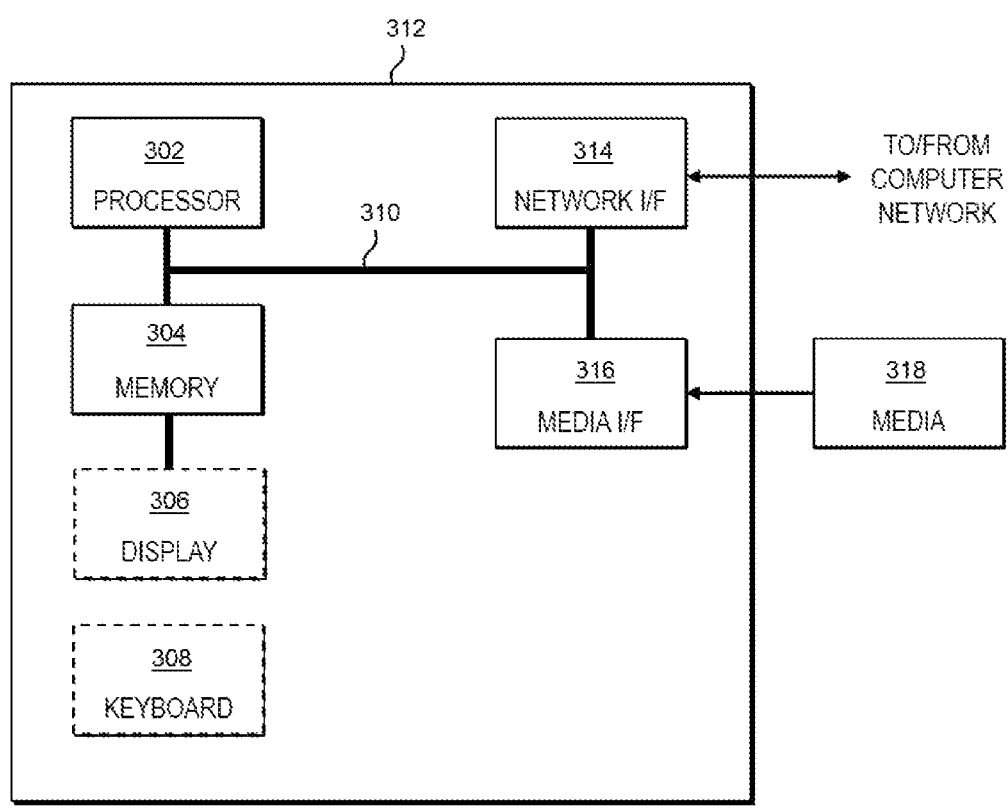
FIG. 3 depicts a computer system that may be useful in implementing one or more aspects and/or elements of the invention.

One or more embodiments can make use of software running on a general purpose computer or workstation. With reference to FIG. 3, such an implementation might employ, for example, a processor 302, a memory 304, and an input/output interface formed, for example, by a display 306 and a keyboard 308. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, one or more mechanisms for inputting data to the processing unit (for example, mouse), and one or more mechanisms for providing results associated with the processing unit (for example, printer). The processor 302, memory 304, and input/output interface such as display 306 and keyboard 308 can be interconnected, for example, via bus 310 as part of a data processing unit 312. Suitable interconnections, for example via bus 310, can also be provided to a network interface 314, such as a network card, which can be provided to interface with a computer network, and to a media interface 316, such as a diskette or CD-ROM drive, which can be provided to interface with media 318.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 302 coupled directly or indirectly to memory elements 304 through a system bus 310. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 308, displays 306, pointing devices, and the like) can be coupled to the system either directly (such as via bus 310) or through intervening I/O controllers (omitted for clarity).

Network adapters such as network interface 314 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 312 as shown in FIG. 3) running a server program. It will be understood that such a physical server may or may not include a display and keyboard.

As noted, aspects of the present invention may take the form of a computer program product embodied in one or more computer readable medium(s) having computer readable program code embodied thereon. Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Media block 418 is a non-limiting example. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the elements depicted in the block diagrams and/or described herein; by way of example and not limitation, a client module and a server module. The method steps can then be carried out using the distinct software modules and/or sub-modules of the system, as described above, executing on one or more hardware processors 302. Further, a computer program product can include a computer-readable storage medium with code adapted to be implemented to carry out one or more method steps described herein, including the provision of the system with the distinct software modules.

In any case, it should be understood that the components illustrated herein may be implemented in various forms of hardware, software, or combinations thereof; for example, application specific integrated circuit(s) (ASICS), functional circuitry, one or more appropriately programmed general purpose digital computers with associated memory, and the like. Given the teachings of the invention provided herein, one of ordinary skill in the related art will be able to contemplate other implementations of the components of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
   receiving one or more crowdsourced reports about one or more environmental conditions, the one or more crowdsourced reports being obtained over a network infrastructure from a plurality of distributed user devices;

inferring one or more input parameters for at least one disease outbreak model based at least in part on the one or more crowdsourced reports;

applying the at least one disease outbreak model to at least the one or more inferred parameters to predict one or more characteristics of at least one potential disease outbreak associated with the reported one or more environmental conditions; and based at least in part on the predicted one or more characteristics, implementing one or more corrective actions to mitigate the at least one potential disease outbreak.

2. The method of claim 1, wherein the one or more crowdsourced reports of the one or more environmental conditions are received through at least one client application accessible through at least one of a telephone or a computer.

3. The method of claim 2, wherein the one or more corrective actions comprise providing at least one warning message through the at least one client application.

4. The method of claim 1, wherein the at least one disease outbreak model comprises at least one SEIR model.

5. The method of claim 1, wherein inferring the one or more input parameters for the at least one disease outbreak model comprises correlating the one or more crowdsourced reports with historical data.

6. The method of claim 5, wherein the historical data concerns at least one past disease outbreak.

7. The method of claim 1, wherein the inferred one or more input parameters for the at least one disease outbreak model comprise at least one of:
a probability that the at least one potential disease outbreak may occur;
a time when the at least one potential disease outbreak may occur; and
a location where the at least one potential disease outbreak may occur.

8. The method of claim 1, wherein implementing the one or more corrective actions comprises displaying at least one map showing if and how the at least one potential disease outbreak is likely to spread over time.

9. The method of claim 8, wherein the at least one map is displayed to at least one public health official.

10. The method of claim 8, wherein the at least one map is animated.

11. The method of claim 1, wherein the one or more corrective actions comprises at least one automated release of at least one pesticide.

12. The method of claim 1, further comprising filtering the one or more crowdsourced reports based on whether the reported one or more environmental conditions are associated with the at least one potential disease outbreak.

13. The method of claim 12, wherein the reported one or more environmental conditions are associated with the at least one potential disease outbreak based at least in part on how the reported one or more environmental conditions affect at least one transmission vector associated with the at least one potential disease outbreak.

14. The method of claim 13, wherein the at least one transmission vector comprises at least one of an insect and a rodent.

15. The method of claim 1, further comprising clustering the one or more crowdsourced reports having a similar context.

16. The method of claim 15, wherein the similar context of the one or more crowdsourced reports comprises geographical proximity.

17. The method of claim 15, wherein the similar context of the one or more crowdsourced reports comprises temporal proximity.

18. The method of claim 1, further comprising calibrating one or more predictive models based at least in part on whether the predicted one or more characteristics were correct.

19. A system, comprising at least a first apparatus comprising:
a first memory; and
at least a first processor coupled with the first memory and operative:
to receive one or more crowdsourced reports about one or more environmental conditions, the one or more crowdsourced reports being obtained over a network infrastructure from a plurality of distributed user devices;
to infer one or more input parameters for at least one disease outbreak model based at least in part on the one or more crowdsourced reports;
to apply the at least one disease outbreak model to at least the one or more inferred parameters to predict one or more characteristics of at least one potential disease outbreak associated with the reported one or more environmental conditions; and
based at least in part on the predicted one or more characteristics, to implement one or more corrective actions to mitigate the at least one potential disease outbreak.

20. The system of claim 19, wherein the first apparatus is operative to communicate with a second apparatus, the second apparatus comprising:
a second memory; and
at least a second processor coupled with the first memory and operative:
to execute at least one client application through which a user of the second apparatus generates and transmits the one or more crowdsourced reports of the one or more environmental conditions to the first apparatus.

21. The system of claim 20, wherein the second apparatus comprises a mobile telephone.

22. A computer program product comprising a non-transitory machine-readable storage medium having machine-readable program code embodied therewith, said machine-readable program code comprising:
machine-readable program code configured:
to receive one or more crowdsourced reports about one or more environmental conditions, the one or more crowdsourced reports being obtained over a network infrastructure from a plurality of distributed user devices;
to infer one or more input parameters for at least one disease outbreak model based at least in part on the one or more crowdsourced reports;
to apply the at least one disease outbreak model to at least the one or more inferred parameters to predict one or more characteristics of at least one potential disease outbreak associated with the reported one or more environmental conditions; and
based at least in part on the predicted one or more characteristics, to implement one or more corrective actions to mitigate the at least one potential disease outbreak.

* * * * *